US00PP36296P2

(12) United States Plant Patent
Miller

(10) Patent No.: US PP36,296 P2
(45) Date of Patent: Dec. 3, 2024

(54) ***SALVIA* PLANT NAMED MBN20203A**

(50) Latin Name: *Salvia microphylla*
Varietal Denomination: MBN20203A

(71) Applicant: Luen Miller, Soquel, CA (US)

(72) Inventor: Luen Miller, Soquel, CA (US)

( * ) Notice: Subject to any disclaimer, the term of this patent is extended or adjusted under 35 U.S.C. 154(b) by 0 days.

(21) Appl. No.: 18/532,446

(22) Filed: Dec. 7, 2023

(51) Int. Cl.
*A01H 5/02* (2018.01)
*A01H 6/50* (2018.01)

(52) U.S. Cl.
USPC ..... Plt./475

(58) Field of Classification Search
USPC ..... Plt./263.1, 475
See application file for complete search history.

*Primary Examiner* — Karen M Redden
(74) *Attorney, Agent, or Firm* — Cassandra Bright

(57) ABSTRACT

A new and distinct *Salvia microphylla* cultivar named 'MBN20203A' is disclosed, characterized by variegated foliage on plants which are very compact and dense and have greyed-purple flower stalks. Flowers and flower buds are dark magenta with a distinct purple hue. The new cultivar is a *Salvia*, typically suited for ornamental garden use, or as a cut flower.

1 Drawing Sheet

Latin name of the genus and species: *Salvia microphylla*.
Variety denomination: 'MBN20203A'.

BACKGROUND OF THE INVENTION

The new variety originated as a chance discover by the inventor, Luen Miller. The variety was discovered as a naturally occurring branch mutation on a single plant of *Salvia microphylla* 'Dazzler', unpatented. The new variety was discovered during August of 2017 at a commercial nursery in Royal Oaks, California in a commercial planting of the parent variety.

After selecting and isolating the new cultivar, asexual reproduction of the new cultivar 'MBN20203A' was first performed at a commercial nursery in Royal Oaks, California in September of 2017. Vegetative terminal cuttings were used for propagation. The inventor continued confidential, controlled evaluation and propagation of 'MBN20203A', to establish a stable clone. 'MBN20203A' has since produced eight generations and has shown that the unique features of this cultivar are stable and reproduced true to type. Typical asexual reproduction of the new variety is by softwood vegetative cuttings.

SUMMARY OF THE INVENTION

The cultivar 'MBN20203A' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'MBN20203A'. These characteristics in combination distinguish 'MBN20203A' as a new and distinct *Salvia* cultivar:

1. Variegated foliage.
2. Dark magenta flowers with a purple hue.
3. Flower buds with purple tinge.
4. Greyed-purple flower stalks.

5. Very compact, dense plants.

PARENTAL COMPARISON

Plants of the new cultivar 'MBN20203A' are similar to the parent in most horticultural characteristics. However, 'MBN20203A' differs in the following:

1. The new variety has variegated foliage; the parent variety has solid colored foliage.
2. Plants of the new variety are more compact and dense than plants of the parent variety.

COMMERCIAL COMPARISON

Plants of the new cultivar 'MBN20203A' can be compared to the commercial variety *Salvia* 'Variegata', U.S. Plant Pat. No. 8,560. Plants of 'MBN20203A' are similar to plants of 'Desert Blaze' in most horticultural characteristics, however, plants of 'MBN20203A' differ in the following:

1. Foliage of the new variety is variegated through the leaf blade; foliage of 'Variegata' is mainly variegated along the margin.
2. Plants of the new variety are more compact and dense than plants of 'Variegata'.
3. Plants of the new variety begin blooming 4 to 6 weeks earlier in Spring than plants of 'Variegata'.

Plants of the new cultivar 'MBN20203A' can be compared to *Salvia* 'Killer Cranberry', U.S. Plant Pat. No. 26,609. The new variety is similar in several horticultural characteristics. However, the plants of 'MBN20203A' differ in the following:

1. Foliage of 'Killer Cranberry' is solid green, the new variety has variegated foliage.
2. Height of the new variety is 14 cm to the top of the foliage plane and 20 cm to the top of the flowering plane; this comparator averages 30 cm to the top of the foliar plant and 50 cm to the top of the flowering plane.

BRIEF DESCRIPTION OF THE PHOTOGRAPH

The accompanying photograph illustrates a plant of the new variety at approximately 10 months of age, grown in Royal Oaks, CA. The photograph was taken using conventional techniques and although colors may appear different from actual colors due to light reflectance it is as accurate as possible by conventional photographic techniques. Age of the plant

DETAILED BOTANICAL DESCRIPTION

In the following description, color references are made to The Royal Horticultural Society Colour Chart, 2007, except where general terms of ordinary dictionary significance are used. The following observations and measurements describe 'MBN20203A' plants grown at a commercial nursery in Royal Oaks, California, under bright, unshaded conditions. Average day temperatures were approximately 8° C. to 26° C. and the average night temperature was approximately 3° C. to 18° C. No artificial light, photoperiodic treatments or chemical treatments were given to the plants. Measurements and numerical values represent averages of typical plant types.

Botanical classification: *Salvia microphylla* 'MBN20203A'.

Age of the plant described: Approximately 8 months.

Container size of the plant described: 1-gallon commercial container.

ROOTS

Root description: Fine, densely fibrous. Colors include Green-White 157D on new growth and Orange-White 159C, Grey-Brown 199B and 199C for older roots.

PLANT

Growth habit: Upright and somewhat outwardly angled. Compact.

Height: Approximately 14 cm to top of foliage. Approximately 20 cm to top of flowering plane. Measured from soil level of pot.

Plant spread: Approximately 28 cm.

Growth rate: Rapid.

Branching characteristics: Very well branched. Approximately 4 to 6 branches emerging from a pinch, which branch into another 4 to 6 primary lateral branches.

Length of primary lateral branches: Approximately 8 to 18 cm.

Diameter of lateral branches: Approximately 0.35 cm

Quantity of lateral branches: About 18 to 32.

Stem:

- *Color*.—New growth: Near RHS Yellow-Green 144A. Mature growth: Near RHS Yellow-Green 144A and 144B, striped Greyed-Purple 187A.
- *Texture*.—Slightly hirsute and moderately ribbed. Older growth slightly scaly.

Internode length: Average range 3.5 to 4.5 cm.

FOLIAGE

Leaf:

- *Arrangement*.—Opposite.
- *Quantity*.—Average range 8 to 12 fully expanded and 6 to 12 immature leaves per main branch.
- *Average length*.—Approximately 1.7 cm to 2.2 including petiole.
- *Average width*.—Approximately 1.0 cm to 1.2 cm.
- *Shape of blade*.—Ovate.
- *Apex*.—Acute.
- *Base*.—Broad attenuate, nearly truncate
- *Attachment*.—Stalked.
- *Margin*.—Crenate.
- *Texture of top surface*.—Matte, rough. Finely reticulated.
- *Texture of bottom surface*.—Matte, glabrous. Prominent reticulated veins.
- *Color*.—Young foliage upper side: Near RHS Green 137A with distinct areas of Yellow 8C throughout leaf blade. Young foliage under side: Near RHS Green 138A with distinct areas of Yellow 11D throughout leaf blade. Mature foliage upper side: Near RHS Green 137A with distinct areas of Yellow 8C throughout leaf blade. Mature foliage under side: Near RHS Green 138A with distinct areas of Yellow 11D throughout leaf blade.
- *Venation*.—Type: Reticulate. Venation color upper side: Near RHS Green 138B. Venation color under side: Near RHS Green 138B.
- *Petiole*.—Average Length: Average range 2 to 4 mm. Diameter: Approximately 2 mm. Color: Near Green 138A Other: Foliage strongly aromatic.

FLOWER

Natural flowering season: Flowering from early Spring until Fall.

Inflorescence type and habit: Flowers arranged in verticillasters on spikes.

Flower longevity on plant: Individual flowers last approximately 7 to 10 days on the plant. Each spike lasts approximately 6 to 8 weeks with flowers. Corolla self-cleaning, calyx persistent.

Quantity of flowers: About 6 to 10 buds and 6 to 12 fully opened flowers per spike, at one time. Mature plants have approximately 50 to 70 spikes.

Spike size:

- *Diameter*.—Approximately 3.5 cm.
- *Height*.—Approximately 7.0 to 11.0 cm.

Individual flowers:

Size:

- *Diameter*.—Approximately 1.6 cm.
- *Length*.—Approximately 2.8 cm.

Fragrance: Moderate, herbaceous scent.

Corolla:

- *Petal arrangement*.—The corolla is sympetalous and typically bilabiate with 2 small, fully fused lobes forming a single upper lip and 3 larger fused lobes forming a lower lip.
- *Margin*.—Entire.
- *Tip shape*.—Upper lip tip obtuse, lower lip tip retuse.
- *Length*.—Upper lip Approximately 1.1 cm. Lower lip Approximately 1.4 cm. Tube length Approximately 1.6 cm.
- *Width*.—Upper lip: Approximately 0.4 cm. Lower lip Approximately 1.5 cm. Tube width: Approximately 0.6 cm.
- *Texture*.—Upper lip: Glabrous interior, pubescent exterior. Slightly sticky. Lower lip: Glabrous all surfaces.

Color:

- *Upper lip*.—When opening: Inner surface: Near RHS Red-Purple N74C. Outer surface: Near RHS Red-Purple 72A. Fully opened: Inner surface: Near RHS Red-Purple 70B.

Color:

*Lower lip*.—When opening: Upper surface: Near RHS Red-Purple 61B with a slight flush 61A. Under surface: Near RHS Red-Purple 64C flushed 64B. Fully opened: Upper surface: Near RHS Red-Purple 64B flushed N74B. Under surface: Near RHS Red-Purple 64B margin flushed N74B. Central section near Purple 76D.

Color:

*Tube*.—When opening: Inner surface: Near RHS Red-Purple N74C lightly streaked Purple 76C. Base White N155D. Outer surface: Near RHS Red-Purple 64A lightly streaked N74B. Base White N155D. Fully opened: Inner surface: Near RHS Red-Purple 70D lightly streaked Purple 76C. Base White N155D. Outer surface: Near RHS Red-Purple 70A lightly streaked N74A. Base White N155D.

Bud: Flower bud includes immature calyx which completely surrounds immature corolla.

*Shape*.—Ovoid.
*Length*.—Approximately 1.4 cm.
*Diameter*.—Approximately 0.4 cm.
*Color*.—Near RHS Red-Purple 71A with Purple 77A flush.

Calyx:

*Length*.—Approximately 1.0 cm.
*Diameter*.—Approximately 5 mm.
*Shape*.—Tubular.

Sepals:

*Shape*.—Quantity per flower: 3, fused to form a tube. Unfused apex.
*Length*.—Approximately 4 mm unfused portion.
*Width*.—Approximately 3 to 4 mm.
*Margin*.—Entire.
*Apex*.—Short apiculate.
*Texture*.—Slightly hirsute and ridged.
*Color*.—Immature: Near Yellow-Green 147B, well defined stripes near Greyed-Purple N187A. Mature: Near Yellow-Green 146A, well defined stripes near Greyed-Purple N187A.

Peduncle:

*Length*.—Average 2.5 cm.
*Diameter*.—3 mm.
*Color*.—Near RHS Yellow-Green 146A, lightly flushed Greyed-Purple N186B.
*Orientation*.—Straight or very slightly curved. Occurring at approximately 15 degree angle from center of plant.
*Strength*.—Moderately strong.
*Texture*.—Slightly hirsute, ridged.

Pedicels:

*Length*.—Average 2 mm.
*Diameter*.—1 mm.
*Color*.—Near RHS Greyed-Purple N186A.
*Orientation*.—Straight, approximately 15 degree angle from attachment.
*Strength*.—Strong.
*Texture*.—Hirsute.

REPRODUCTIVE ORGANS

Stamens:

*Number*.—2.
*Filament length*.—Approximately 4 mm.
*Filament color*.—Near RHS White N155B.

Anthers:

*Shape*.—Linear
*Length*.—1 mm.
*Color*.—Near RHS Red-Purple 64A.
*Pollen*.—Not observed.

Pistil:

*Number*.—1.
*Length*.—Approximately 2.5 cm.
*Style*.—Length: Approximately 2.1 cm. Color: Near RHS White N155D, flushed Red-Purple 64C.
*Stigma*.—Shape: Forked. Color: Near RHS Red-Purple 71A. Ovary: Colored near RHS Yellow-Green 145D, oblong, approximately 2 mm long and 1 mm in diameter.

OTHER CHARACTERISTICS

Seeds and fruits: No seeds/fruits observed.

Disease/pest resistance: Neither resistance nor susceptibility to pathogens and pests common to *Salvia microphylla* have been observed.

Temperature tolerance: The new variety tolerates temperatures within USDA zones 7 to 9.

What is claimed is:

1. A new and distinct cultivar of *Salvia* plant named 'MBN20203A' as herein illustrated and described.

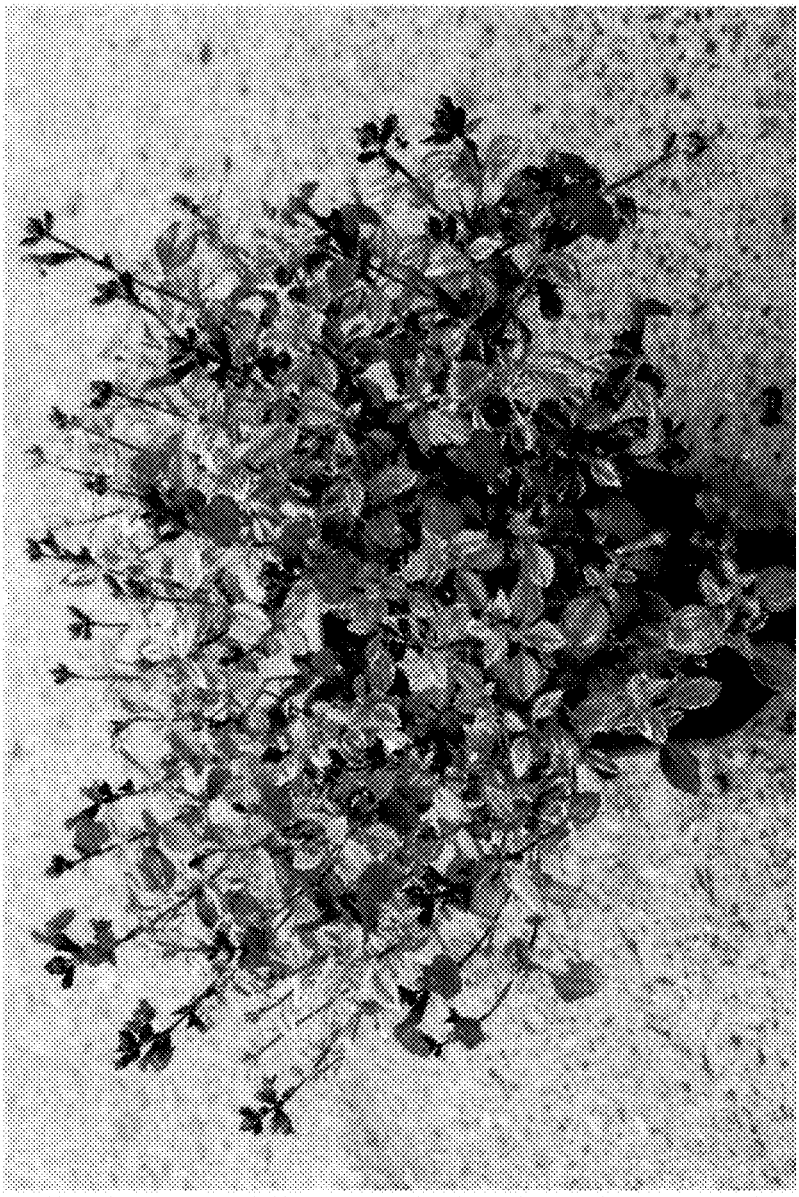

* * * * *